United States Patent
Pham et al.

(10) Patent No.: US 6,991,799 B2
(45) Date of Patent: Jan. 31, 2006

(54) NON-STICKY COSMETIC MOISTURIZER FOR SKIN AND HAIR

(75) Inventors: Quynh T. Pham, Murray Hill, NJ (US); Tak Yu Lam, Brooklyn, NY (US); Norman Kramer Richardson, Rockaway, NJ (US); Prem Chandar, Closter, NJ (US); Alexander Lips, Edgewater, NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 77 days.

(21) Appl. No.: 10/044,856

(22) Filed: Nov. 1, 2001

(65) Prior Publication Data

US 2002/0131946 A1   Sep. 19, 2002

Related U.S. Application Data

(60) Provisional application No. 60/252,703, filed on Nov. 22, 2000.

(51) Int. Cl.
*A61K 7/00* (2006.01)
*A61K 7/06* (2006.01)
*A61K 7/075* (2006.01)
*A61K 7/08* (2006.01)

(52) U.S. Cl. ............... 424/401; 424/70.1; 424/70.21; 424/70.22; 424/70.31

(58) Field of Classification Search ............ 424/70.1, 424/401, 70.21, 70.22, 70.31
See application file for complete search history.

(56) References Cited

U.S. PATENT DOCUMENTS

| | | | | |
|---|---|---|---|---|
| 4,952,560 A | * | 8/1990 | Kigasawa et al. | 514/2 |
| 5,063,057 A | * | 11/1991 | Spellman et al. | 424/401 |
| 5,128,123 A | * | 7/1992 | Brewster et al. | 424/65 |
| 5,209,925 A | | 5/1993 | Lindauer et al. | |
| 5,858,340 A | | 1/1999 | Briggs et al. | |
| 6,033,680 A | | 3/2000 | Dixon et al. | |
| 6,294,186 B1 | * | 9/2001 | Beerse et al. | 424/405 |
| 6,436,413 B1 | * | 8/2002 | Gers-Barlag et al. | 424/401 |

FOREIGN PATENT DOCUMENTS

| | | |
|---|---|---|
| EP | 1 208 835 A3 | 4/2003 |
| FR | 2 787 322 A | 6/2000 |
| JP | 59 209635 | 11/1984 |
| JP | 63216815 | * 9/1988 |
| JP | 63313709 | * 12/1988 |
| JP | 2001309986 | * 11/2001 |
| WO | 91/11171 | 8/1991 |
| WO | 92/19216 | 12/1992 |
| WO | 92/19275 | 12/1992 |

OTHER PUBLICATIONS

"Polymers For Personal Care" BF Goodrich, TDS-114 Revision dated May 1998.
"Contact Angles and Wettability of Human Skin", Hans Schott, *J. of Pharmaceutical Sciences*, vol. 60, No. 12, 1893-1895 (1971).
Database Derwent WPI Acct. No. 1985-014615/198503.

* cited by examiner

*Primary Examiner*—Thurman K. Page
*Assistant Examiner*—Blessing Fubara
(74) *Attorney, Agent, or Firm*—Ellen Plotkin

(57) ABSTRACT

A non-sticky moisturizing cosmetic composition containing a relatively high level of a humectant, such as glycerol or sorbitol, and a polymeric wetting agent.

5 Claims, No Drawings

NON-STICKY COSMETIC MOISTURIZER FOR SKIN AND HAIR

This application claims the benefit of U.S. provisional application No. 60/252,703, filed on Nov. 22, 2000.

FIELD OF THE INVENTION

The present invention relates to a cosmetic composition for skin and hair which delivers a moisturizing effect, without a sticky sensation.

BACKGROUND OF THE INVENTION

Humectants, such as glycerol and sorbitol, are known as excellent moisturizers for skin, scalp and hair. See for instance WO9111171, WO9219216, WO9219275 and U.S. Pat. No. 5,858,340. The moisturizing capabilities of these ingredients are concentration dependent. Unfortunately, when incorporated into formulations at concentrations above 10%, they confer a sticky, tacky feeling. Due to this unpleasant consumer sensory experience formulations containing higher levels of humectants are, for the most part, not commercially acceptable. The need exists for commercially acceptable moisturizing compositions containing higher levels of humectants.

SUMMARY OF THE INVENTION

A cosmetic non-sticky moisturizer for skin and hair comprising:
 (a) at least about 10% by weight of the composition of a polyhydric alcohol humectant;
 (b) about 0.01% to about 10% of a polymeric wetting agent which forms a uniform film in a Wetting Test;
 (c) a cosmetically acceptable vehicle.

The polymeric wetting agent may be an amphipathic block copolymer, a polymer containing a hydrophilic backbone modified with hydrophobic groups, or mixtures thereof.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

The term "skin" as used herein includes the skin on the face, neck, chest, back, arms, hands, legs and scalp.

Humectant

The humectant is included in the inventive compositions to deliver a moisturizing benefit to the skin. Suitable humectants are polyhydric alcohols and include, but are not limited to glycerol (a.k.a. glycerine), humectants other than glycerine which can be added herein include (sorbitol, propylene glycol, butylene glycol, hexylene glycol, ethoxylated glucose and hexantriol). The humectant is included in the inventive compositions at a concentration of at least 10%. Preferably the concentration of at least 10%, generally in the range about 10% to about 90%, preferably about 10% to about 60%, most preferably to optimize the moisturizer benefits, about 10% to about 35%. The most preferred humectants are glycerol and sorbitol due to their low cost and high efficacy.

Polymeric Wetting Agent

A polymeric wetting agent is included in the inventive compositions to attain the spreading of the moisturizing agent and the inventive compositions. The polymeric wetting agent is selected for inclusion in the inventive compositions by testing the polymer in a Wetting Test.

Wetting Test

A. Sample
  Polymer at concentration of 0.25 weight % is dissolved in glycerol. Glycerol may be present either alone or with water. If used with water, then glycerol-water solution is at 30% glycerol. These polymer solutions are made at temperatures of about 20° to about 80° C. and allowed to dissolve overnight.
 B. Substrate
  A suitable substrate is defined as a synthetic or natural surface with a critical wetting tension of $20 \times 10^{-3}$ to $30 \times 10^{-3}$ N/m. The critical wetting tension is measured according to procedure published in "Contact Angles and Wettability of Human Skin," by Hans Schott, in *Journal of Pharmaceutical Science* Vol. 60, No. 12, 1893–1895, December 1971.
  Examples of suitable substrates with measured critical wetting tensions are

| | |
|---|---|
| Vitro-Skin (IMS Inc.) | $25 \times 10^{-3}$ N/m |
| Transparency films (3M, Avery, Apollo) | $20 \times 10^{-3}$ N/m |
| Human arm skin | $27 \times 10^{-3}$ to $29 \times 10^{-3}$ N/m |

C. Measurement Procedure
  1. Apply 0.8 milliliter of sample on substrate at room temperature (20–25° C.)
  2. Spread sample by rubbing in circular motion for 15 seconds over an area of 20 cm²
  3. Five minutes after rubbing, spreading is judged visually following these criteria
   a. complete spreading/uniform film=the sample forms an even coating over the rub-in area (20 cm²)
   b. partial wetting=(1) large macroscopic (air) holes (>1 millimeter in diameter) develops in the film or (2) the film breaks into numerous macroscopic drops (>1 millimeter in diameter)
   c. dewetting=the sample retracts back into a drop when rubbing motion ceased A glycerol wetting agent meets criterium (a) only. For example, PEMULEN TR-2 amphiphatic block copolymer meets (a), PEMULEN TR-1 falls under (c), and CARBOPOL 981 is (b).

Suitable polymeric wetting agents generally fall within the following two classes:
 (b1) an amphipathic block copolymer;
 (b2) a polymer containing a hydrophilic backbone modified with hydrophobic groups.

The block copolymers can be either diblocks (AB architecture) or triblocks (ABA or BAB architectures). For illustration, the A block is hydrophilic, e.g. polyethylene oxide, polyacrylamide, polyacrylic acid, siloxane, guar, and biopolymers (gum arabic, protein, gelatin). The B block is hydrophobic, e.g. polypropylene oxide, polyisobutylene, and polystyrene.

For hydrophobically modified polymers, the main component or backbone is hydrophilic. Along this backbone and/or at the terminal ends, hydrophobic groups (e.g. alkanes (C12 to C30)) are grafted. These polymers are produced by BASF, ISP, Aqualon/Hercules, BF Goodrich etc. under the category of polymeric emulsifiers.

These molecules are predominantly hydrophilic and can be solubilized in a polar solvent (water, glycerol). However, the polymers also contain sufficient hydrophobic domains that allow the polymers to adsorb or "stick" on hydrophobic surfaces. These two characteristics are keys to the formation of a uniform thin film of the humectant on skin. Tables A and B contain examples of polymers that did or did not, respectively, form a uniform film in a Wetting Test.

TABLE A

Polymers that formed a uniform film in a Wetting Test

| Source | Polymer Trade Name | Polymer Conc. (% wt) | Glycerol Conc. (% wt) |
|---|---|---|---|
| BASF | PLURONIC F38 | 0.25 | 99.75 |
| BASF | PLURONIC F68 | 0.25 | 99.75 |
| BF Goodrich | PEMULEN TR2 | 0.25 | 99.75 |
| BF Goodrich | PEMULEN TR2 | 0.25 | 30 |

TABLE B

Polymers that did not form a uniform film in a Wetting Test

| Source | Polymer Trade Name | Polymer Conc. (% wt) | Glycerol Conc. (% wt) |
|---|---|---|---|
| BASF | PLURONIC L101 | 0.25 | 99.75 |
| BASF | PLURONIC L121 | 0.25 | 99.75 |
| BF Goodrich | PEMULEN TR1 | 0.25 | 99.75 |
| BF Goodrich | CARBOPOL 981 | 0.25 | 99.75 |
| Methylcellulose | BENECEL | 0.25 | 99.75 |
| Hydroxyethylcellulose | NATROSOL | 0.25 | 99.75 |
| Hydroxypropylcellulose | KLUCEL | 0.25 | 99.75 |

The wetting agent is included in the inventive compositions in the concentration of from 0.01% to 10%, preferably to optimize ratios of wetting agent and glycerol content for uniform spreading and non-sticky feel, from 0.01% to 2%, most preferably in order to deliver non-sticky feel without being too viscous, from 0.1% to 2%. The most preferred wetting agents are PEMULEN TR-2 and PLURONIC F38, because they are cosmetically acceptable raw materials, sufficiently hydrophobic to stick to skin.

Elastomer

An elastomer is a preferred optional ingredient for inclusion in the inventive compositions. Elastomers impart silkiness. These materials are blends of highly crosslinked siloxane polymers and silicone oils. Supplier sources include GE Silicones (Waterford, N.Y.), Dow Corning (Midland, Mich.), and Rhodia Silicones (Cranbury, N.J.). Elastomers are preferably included in an amount of about 0.01% to about 30%, preferably about 1% to about 25%, most preferably about 5% to about 15%. Most preferably, to help disperse the elastomer uniformly in the formulations, the elastomer is included in combination with additional volatile silicone oils (cyclomethicones and dimethicones). In that case, the volatile silicone oil is included in an amount of about 0% to about 25%, preferably about 1% to about 5%.

TABLE C

Examples of suitable elastomers

| Trade Name | Source | CTFA Name | Ingredients |
|---|---|---|---|
| Silicone Elastomer Dispersion SFE839 | GE Silicones (Waterford, NY) | cyclopentasiloxane and dimethicone/vinyl dimethicone crosspolymer | decamethyl cyclopenta siloxane, polydimethyl siloxane, octamethylcyclotetra siloxane, and mixed cyclosiloxanes |
| Silicone Elastomer Blend 9040 | Dow Corning (Midland, MI) | cyclomethicone and dimethicone crosspolymer | decamethyl cyclopenta siloxane, dimethyl methylalkenyl siloxane, and dimethyl cyclosiloxanes |
| Rhodorsil Fluids 47 | Rhodia Silicones (Cranbury, NJ) | polydimethylsiloxane | polydimethylsiloxanes |

Crystalline Fatty Acid

The crystalline fatty acid is a preferred optional ingredient for skin feel, consistency, and occlusion. Preferably, the fatty acid contains from 12 to 22 carbon atoms, because such acids are cheap and the most aesthetically acceptable. The most preferred fatty acid is stearic acid. The term "acid" as employed herein does not exclude the presence of a salt of fatty acid depending on the pH of the final composition. For instance, sodium, potassium or ammonium salts may be present. The salt amount is included in the amount of fatty acid. The inventive compositions preferably contain at least 0.25% of fatty acid, most preferably about 0.25% to about 18%.

Oil

An oil is preferably included in the inventive compositions for skin feel and emolliency.

Suitable fluid oils include but are not limited to esters of fatty acids or alcohols and hydrocarbons, preferably monoesters of fatty acids or alcohols, as long as they satisfy the solubility requirements described herein. Most preferably, fluid oil is selected from the group consisting of isostearyl palmitate, tridecyl salicylate, C12–15 octanoate, isopropyl stearate, isopropyl myristate and isopropyl palmitate, or any mixtures thereof. Dicapryl ether, such as with a trade name CETIO OE, is also included as most preferable oil.

The oil is preferably included in an amount of about 0.1% to about 30%, most preferably in an amount of about 1% to about 15%.

Neutralizing Agent

A neutralizing agent is preferably included in the inventive compositions to neutralize fatty acids, thereby building viscosity and stabilizing emulsion structure. Suitable neutralizing agents include but are not limited to triethanolamine, potassium hydroxide, sodium hydroxide, ammonium hydroxide, amino methyl propanol ethanolamine. The neutralizing agent is preferably included in an amount of about 0% to about 5%, most preferably in an amount of about 0.05% to about 1%.

Further Optional Ingredients

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, skin lightening agents, tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, PARSOL MCX and BENZOPHENONE-3, respectively.

The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, Y-linolenic acid, homo-Y-linolenic acid, columbinic acid, eicosa-(n-6, 9,13)-trienoic acid, arachidonic acid, Y-linolenic acid, timnodonic acid, hexaenoic acid and mixtures thereof.

Other optional ingredients may include coloring agents, opacifiers and pigments (e.g. titanium dioxide, silica) and perfumes. Amounts of these materials may range anywhere from 0.001% up to 20% by weight of the composition.

Cosmetically Acceptable Vehicle

The composition according to the invention also comprises a cosmetically acceptable vehicle to act as a dilutant, dispersant or carrier for the active components in the composition, so as to facilitate their distribution when the composition is applied to the skin or hair.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Coming Company under the 200 and 550 Series. Amounts of silicone which can be utilized in the compositions of this invention range anywhere from 5 to 95%, preferably from 25 to 90% by weight of the composition.

Use of the Composition

The composition according to the invention is intended primarily as a product for topical application to human skin or hair, especially as an agent for conditioning and smoothening the skin, and preventing or reducing the appearance of wrinkled or aged skin or dry hair.

In use, a small quantity of the composition, for example from 1 to 5 ml, is applied to exposed areas of the skin or hair, from a suitable container or applicator and, if necessary, it is then spread over and/or rubbed into the skin or hair using the hand or fingers or a suitable device.

Product Form and Packaging

The composition can be packaged in a suitable container to suit its viscosity and intended use by the consumer. For example, a composition can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

EXAMPLE 1

The formulations detailed below in Tables 1 and 2 were prepared using the following procedures:
1. All preparation was performed at room temperature using overhead mixers (1000 rpm)
2. 2% aqueous solution of Pemulen TR2 and neutralizer was prepared and allowed time to hydrate polymer completely
3. oil phase containing elastomer, silicone oil, and any other oils was prepared
4. water and glycerol were mixed, then 2% Pemulen solution added and mixed thoroughly.
5. oil phase was then added Formulation Process with Fatty Acids (Stearic, Behewic):
(a) Fatty acid was heated at 85 to 90° C. and stirred at 1000 rpm
(b) Using another breaker, half the amount of water and half the amount of glycerol were mixed at 90° C. with fatty acid at 90° C.
(c) Triethanolamine was added to adjust pH to 5.5
(d) Upon start of cooling, the remaining water, glycerol, Pemulen TR2 were mixed-in at room temperature and added to above mixture at 40° C.
(e) IPM/Petrolatum were premixed and added to the main mixture drop by drop Compositions 1A–1C in Table 1 contained a polymeric wetting agent and thus were within the scope of the invention. Compositions 2A–2C did not contain a polymeric wetting agent and thus were outside the scope of the invention.

TABLE 1

| Ingredient and Concentration (%) | 1A | 1B | 1C |
|---|---|---|---|
| Water | 63.00 | 64.25 | 63.75 |
| Pemulen TR II | 1.50 | 0.25 | 0.25 |
| Glycerin | 35.00 | 35.00 | 35.00 |
| Glydant DMDM Hydantoin | 0.50 | 0.50 | 1.00 |
| wetting test | uniform film | uniform film | uniform film |

TABLE 2

COMPARATIVE

| Ingredient and % Concentration | 2A | 2B | 2C |
|---|---|---|---|
| Water | 69.25 | 64.25 | 0 |
| Glycerin | 30 | 35 | 99.75 |
| Glydant DMDM Hydantoin | 0.5 | 0.5 | 0 |
| Carbopol 981 | 0.25 | 0.25 | 0.25 |
| wetting test | dewet | dewet partial | dewet |

It can be seen from the comparison of the test results in Tables 1 and 2 that compositions within the scope of the invention delivered a uniform film to the substrate.

EXAMPLE 2

Further compositions within the scope of the invention were prepared, as detailed in Tables 3 and 4.

TABLE 3

| Ingredient and % Conc | 3A | 3B | 3C | 3D | 3E |
|---|---|---|---|---|---|
| Water | 49.25–29.25 | 44.75 | 33.95 | 38.95 | 42.7 |
| Preservative | 0.5 | 0.5 | 0.5 | 0.5 | 0.5 |
| Glycerin | 30 | 35 | 35 | 35 | 35 |
| Pemulen TR 2 | 0.25 | 0.25 | 0.25 | 0.25 | 0.25 |
| TEA (neutralizer) | | | 0.3 | 0.3 | 0.3 |
| Silicone 9040 (Dow) | 20–40 | | | | |
| SFE 839 (GE) | | 15 | 25 | | |
| Dow Corning 2-5513 AMS | | | | 5 | |
| Rhodorsil Fluid 47 V 600,000 | | | | | 1.25 |
| Silicone oil 245 | 0–20 | 5 | 5 | 20 | |
| Silicone oil Mirasil CM4 | | | | | 20 |

TABLE 4

| Ingredient and % Conc | 4A | 4B | 4C |
|---|---|---|---|
| Water | 76.05 | 69.55 | up to 80 |
| Glydant DMDM Hydantoin | 0.2 | 0.2 | 0.2 |
| Glycerin | 15 | 15 | 15–30 |
| Pemulen TR 2 | 0.25 | 0.25 | 0.25 |
| TEA | 0.25 | | |
| IPM | 0.3 | | |
| Petrolatum | 0.075 | | |
| Stearic acid | 7 | 0.7 | 0.7 |
| Sodium stearoyl lactylate | 0.875 | | |
| Sodium stearate | | 0.3 | 0.3 |
| Transcutol | | 5 | 1–5 |
| Cholesterol | | 2 | 2 |
| Lecithin or Sucrose stearate | | 1 | 0–1 |
| SFE 839 (GE) | | 5 | 5–25 |
| Silicone 245 | | 1 | 1–5 |

EXAMPLE 3

The effect of increased humectant concentration on the perception of stickiness was evaluated in a sensory panel.

Each panelist tried two products for each evaluation (one on each hand). The panelist scored stickiness based on a scale of 1 to 10 (1=not at all sticky; 5=moderately sticky; 10=extremely sticky) and also comparatively between the two products. A sample evaluation sheet is shown here. Comparison can only be made for product pairs evaluated at the same time; we take the difference of the scores, and average over six panelists.

One milliliter of product was dispensed with a pipette on the back of the panelist's hand. The panelist then rubbed and spread out the product for 15 seconds, waited for one minute (as product film dried), then evaluated for stickiness.

The formulations evaluated were as follows:

TABLE 5

| Formulation Ingredient and Concentration (%) | 5A - COMPARATIVE A | 5B - COMPARATIVE B |
|---|---|---|
| Water | 79.01 | 49.51 |
| Glycerin | 5.5 | 35 |
| Disodium EDTA | 0.05 | 0.05 |
| Veegum | 0.2 | 0.2 |
| Titanium dioxide 328 | 0.1 | 0.1 |
| Urea USP | 0.01 | 0.01 |
| Carbopol 981 (2% solution) | 3 | 3 |
| Triethanolamine | 1.4 | 1.4 |

TABLE 5-continued

| Formulation Ingredient and Concentration (%) | 5A - COMPARATIVE A | 5B - COMPARATIVE B |
|---|---|---|
| Pristerene 4911 | 2.54 | 2.54 |
| Cerasynt IP | 1.5 | 1.5 |
| Glycerol monostearate | 0.7 | 0.7 |
| Cetyl alcohol and other co-emulsifiers | 1 | 1 |
| Sunflower seed oil | 2 | 2 |
| Silicone and other oils | 2.25 | 2.25 |
| Glydant DMDM Hydantoin | 0.1 | 0.1 |
| Fragrance | 0.25 | 0.25 |
| D&C Yellow | 0.39 | 0.39 |

Neither formulation contained a polymer wetting agent and thus neither was within the scope of the invention. Stickiness evaluation after product was applied and dried: 8 out of 12 panelists judged composition 5A (35% glycerol) was stickier than composition 5B (5% glycerol). A clinical dryness evaluation, however, showed significant difference (better) in moisturization with increased glycerol concentration.

It can be seen from this Example that an increased concentration of glycerol leads directly to decreased dryness, yet also, unfortunately, increased stickiness.

EXAMPLE 4

The following formulations within the scope of the invention were evaluated for stickiness.

TABLE 6

| Formulation Ingredient and % Conc | 6A | 6B | 6C |
|---|---|---|---|
| Methylparaben | 0.20 | 0.20 | 0.20 |
| Carbomer 981 | 0.10 | 0.10 | |
| Pluronic F38 | | | 0.25 |
| Glycerin | 3.00 | 15.00 | 15.00 |
| Water | 80.90 | 68.90 | 68.85 |
| NaOH 10% | 0.10 | 0.10 | |
| Emulgade PL 68/50 | 2.70 | 2.70 | 2.70 |
| Cetearylalcohol | 1.00 | 1.00 | 1.00 |
| Cetiol OE | 2.00 | 2.00 | 2.00 |
| Cetiol V | 2.00 | 2.00 | 2.00 |
| CCT | 4.00 | 4.00 | 4.00 |
| Cetiol J-600 | 3.00 | 3.00 | 3.00 |
| DC Fluid 200/100 cs | 0.50 | 0.50 | 0.50 |
| Propylparaben | 0.10 | 0.10 | 0.10 |
| Phenoxyethanol | 0.40 | 0.40 | 0.40 |

| Product Pairs | Evaluation Score Difference between Product Pairs |
|---|---|
| 6B vs. 6A | 1.67 |
| 6A vs. 6C | 0.17 |
| 6B vs. 6C | 1.00 |
| 6A vs. 6A | 0.33 |

Comparative stickiness evaluation of product pairs. In the first evaluation, the panel compared prototypes with 15 and 3% glycerol; the high (positive) score difference indicates that 15% glycerol is much stickier than the 3%. The second and third evaluations compared the effect of the wetting polymer Pluronic versus the typical thickener Carbopol; 15% glycerol with Pluronic is much less sticky than 15% glycerol with Carbopol and is as nonsticky as the 3% glycerol formulations.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the inventions be limited only by the scope of the claims which follow, and that such claims be interpreted as broadly as is reasonable. Throughout this application, various publications have been cited. The entireties of each of these publications are hereby incorporated by reference herein.

What is claimed is:

1. A cosmetic non-sticky moisturizer for skin and hair consisting essentially of:
   (a) about 10% to about 90% by weight of the composition of a polyhydric alcohol humectant;
   (b) about 0.01% to about 10% of a polymeric wetting agent which forms a uniform film in a Wetting Test selected from the group consisting of:
      (b1) an amphipathic block copolymer;
      (b2) a polymer containing a hydrophilic backbone modified with hydrophobic groups; and
      (b3) mixtures thereof;
   (c) an elastomer and a volatile silicone oil;
   (d) a cosmetically acceptable vehicle.

2. The composition of claim 1, wherein the composition further optionally includes a fluid oil.

3. The composition of claim 1, wherein the composition further optionally includes a crystalline fatty acid.

4. The composition of claim 1, wherein the polymeric wetting agent is (b2) a polymer containing a hydrophilic backbone modified with hydrophobic groups.

5. The composition of claim 1, wherein the composition further optionally includes an oil.

* * * * *